United States Patent
Lewis, II et al.

(10) Patent No.: US 6,554,981 B2
(45) Date of Patent: *Apr. 29, 2003

(54) HYDROGEN PERMEATION PROBE

(75) Inventors: Arnold L. Lewis, II, Dhahran (SA); John K. Boah, Dhahran (SA)

(73) Assignee: Saudi Arabian Oil Company, Dhahran (SA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/152,570

(22) Filed: Sep. 14, 1998

(65) Prior Publication Data

US 2001/0001439 A1 May 24, 2001

(51) Int. Cl.⁷ ............................................. G01N 27/26
(52) U.S. Cl. ..................... 204/400; 204/404; 205/775
(58) Field of Search ............................. 204/400, 415, 204/406, 404

(56) References Cited

U.S. PATENT DOCUMENTS

| | | | |
|---|---|---|---|
| 2,913,386 A | 11/1959 | Clark Jr. .................. 204/195 |
| 3,278,408 A | 10/1966 | Leonard et al. ........... 204/195 |
| 3,325,378 A | 6/1967 | Greene et al. ................ 204/1 |
| 3,410,778 A * | 11/1968 | Krasberg ................... 204/415 |
| 3,468,781 A | 9/1969 | Lucero ....................... 204/195 |
| 3,753,654 A | 8/1973 | Eggertsen ..................... 23/230 |
| 3,773,641 A * | 11/1973 | Fitterer ....................... 204/423 |
| 3,980,542 A * | 9/1976 | Winslow et al. |
| 4,065,373 A * | 12/1977 | Martin et al. ............... 204/404 |
| 4,092,844 A | 6/1978 | Oertle et al. .................... 73/23 |
| 4,248,599 A | 2/1981 | Mommessin et al. ......... 23/230 |
| 4,627,905 A * | 12/1986 | Garner et al. |
| 4,659,435 A * | 4/1987 | Brothers et al. ............ 204/427 |
| 4,752,360 A * | 6/1988 | Jasinski |
| 5,041,204 A | 8/1991 | Kuhn et al. ................. 204/415 |
| 5,202,011 A | 4/1993 | Kiesele et al. .............. 204/415 |
| 5,205,841 A | 4/1993 | Vaiman .......................... 55/16 |
| 5,346,605 A | 9/1994 | Wolcott et al. ............. 204/412 |
| 5,366,609 A * | 11/1994 | White et al. ................ 204/406 |
| 5,405,513 A | 4/1995 | Lewis, II et al. ........... 204/153 |

* cited by examiner

*Primary Examiner*—T. Tung
(74) *Attorney, Agent, or Firm*—Abelman, Frayne & Schwab

(57) ABSTRACT

A method and corresponding apparatus useful for the in situ measurement of atomic hydrogen permeation into carbon steel from process streams including:

(a) a positively-charged test specimen electrode consisting of a planar member of hydrogen damage-resistant steel alloy having an interior surface, the interior surface being provided with a coating of palladium, and an exterior surface that is placed in contact with the process stream;

(b) a fluid-tight reservoir containing a basic liquid electrolyte solution in communication with the palladium coating of the test specimen electrode;

(c) a negatively charged counter electrode positioned in the electrolyte reservoir proximate the test specimen electrode said reservoir, test specimen electrode and counter electrode constituting a probe assembly;

(d) a mounting assembly for supporting and positioning said probe assembly in contact with a process stream and for receiving electrical conductors joined to said probe assembly; and (e) an electrically non-conductive isolator positioned between said mounting assembly and said probe assembly.

20 Claims, 3 Drawing Sheets

HYDROGEN PERMEATION PROBE

FIELD OF THE INVENTION

The invention relates to the in situ, or field measurement of hydrogen atom permeation into the walls of pipelines and vessels containing process streams and, particularly, petroleum process streams.

BACKGROUND OF THE INVENTION

Every corrosion process involves the two basic chemical reactions of oxidation and reduction. In the case of corrosion of carbon steel, the oxidative reaction that results in the destruction of the steel matrix can be represented as:

$$Fe^{\circ} \rightarrow \rightarrow \rightarrow Fe^{+2} + 2e^{-} \qquad (I)$$

In many petrochemical environments, the concurrent reduction reaction is the formation of atomic hydrogen, $$H^{+} + e^{-} \rightarrow \rightarrow \rightarrow H^{\circ} \qquad (II)$$

Furthermore, in most chemical environments the atoms of hydrogen produced by (II) quickly undergo a reaction to form molecular hydrogen which, for the most part, mixes into the process environment and passes as dissolved gas:

$$2H^{\circ} \rightarrow \rightarrow \rightarrow H_{2(g)} \qquad (III)$$

In the typical cases of general corrosion, the combination reaction forming molecular hydrogen occurs virtually concurrently with the reduction of hydrogen ions to atomic hydrogen. However, there are some chemical environments in which the combination reaction of atomic hydrogen to molecular hydrogen is impeded, which results in a higher concentration or lifetime of individual hydrogen atoms at, or very near the surface of the steel. A chemical environment common in the oil industry which causes this phenomenon is one in which hydrogen sulfide gas is present at a concentration of parts per million or greater levels. The presence of hydrogen cyanide and arsenic in the process stream are also known to cause this type of hydrogen corrosion phenomena to occur.

The presence of hydrogen sulfide in oil and gas production process streams can result in potentially destructive corrosion-related phenomena denominated by the general term hydrogen damage. Hydrogen damage is caused by the permeation of atomic hydrogen into susceptible steels. Molecular hydrogen can become trapped in defects in the steel when highly soluble and mobile atoms of hydrogen that are diffusing through the steel matrix combine. When the molecular hydrogen is trapped in a void in the steel, pressure builds up over time, leading to blisters and cracks. Such hydrogen-induced cracking can eventually result in the failure of the pipeline or vessel.

The presence of hydrogen sulfide increases the number of hydrogen atoms permeating into the steel and therefore increases the potential for hydrogen damage. The adequacy of the measures undertaken to control the hydrogen permeation rate and hydrogen damage in oil production facilities that are sour in nature (i.e., where hydrogen sulfide gas is present), is one of the most significant concerns in the industry.

Various control methods have been used in an effort to counteract the potential damage of atomic hydrogen. Steel alloys have been developed that are resistant or immune to hydrogen damage. These alloys are quite expensive and are not a cost-effective solution for all applications. It is also possible to remove or to reduce the concentration of the hydrogen sulfide that is the catalyst for hydrogen damage by subjecting the crude petroleum to additional processing steps. This so-called sweetening process is used in many locations by the oil industry, but it is not always a cost-effective choice. A third control method is the introduction of chemical inhibitors into the process stream at a very low concentration. Since atomic hydrogen damage is a phenomenon that takes place in the interior of the steel matrix, chemical inhibitors and sweetening processes offer an indirect means of controlling the hydrogen gas formation.

The problem for the field engineer is quite significant, since no matter what atomic hydrogen permeation control method is employed, there are limited means available to enable him to evaluate the effectiveness of the control method chosen.

Several techniques have been developed over the years to measure the amount of atomic hydrogen that permeates steel process piping and vessels. Each of these techniques has limitations that detract from its accuracy and/or usefulness under field conditions existing in the petroleum and petrochemical processing industry.

Various in situ hydrogen probes have been developed that can be inserted into process facilities to measure atomic hydrogen permeation rate by measuring the increase in pressure produced by molecular hydrogen. A typical example of this type of probe is the Model 6400 hydrogen probe manufactured by Rohrback Cosasco. The probe consists of a sealed chamber made of the process facility material that is inserted through a 2" access fitting into the process stream. An external pressure gauge or transducer measures the day-to-day buildup of pressure inside of the sealed probe that results when the atoms of hydrogen that are permeating the probe reach the inner surface where they combine to form molecular hydrogen in the probe chamber. The major disadvantage to this type of device is that the signal-to-noise ratio for pressure measurement of molecular hydrogen buildup caused by atomic hydrogen permeation in a field process environment is low due to the fact that the flux is approximately 6E12 atoms of hydrogen per second per $cm^2$, or less. A typical hydrogen probe such as the Cosasco 6400 has an effective probe surface area of approximately 42 $cm^2$ and a minimum internal volume of approximately 20 $cm^3$. This means that the measured pressure increase for this type of probe, under these conditions, will be less than 0.3 psi per day which is below the limit of detection for most pressure gauges or transducers. An additional consideration is the variation of internal pressure of a closed container due to temperature fluctuations. A ten degree variation in temperature will result in an observed pressure fluctuation of approximately 0.5 psi. It would not be possible to obtain reliable process information on a system at these levels at less than one week intervals.

Electrochemical measurement devices known as "patch probes" are designed to be attached to the exterior of the vessel being monitored. Their method of operation assumes that atoms of hydrogen which enter into the steel from the inside will eventually find their way to the exterior wall where they can be measured. They suffer from several limitations.

First, if the metal of the process vessel is susceptible to hydrogen damage (it must be assumed that it is or there would be no need to monitor it), then a certain fraction of the hydrogen atoms that enter the steel matrix will remain trapped there as molecular hydrogen leading to hydrogen damage. The entrainment of this hydrogen gas will result in fewer atoms of hydrogen reaching the external surface of the process vessel and consequently a smaller and nonreproducible signal available from the patch probe.

Additional problems arise from the method of measurement, which is to oxidize the atoms of hydrogen as soon as they appear at the external surface of the process vessel walls. The oxidation is therefore being performed at the surface of the steel walls of the process vessel. First, it has been shown that the efficiency of oxidizing hydrogen atoms from the surface of steel in this environment is only 20%. Since the signals are small to begin with, an 80% signal loss is catastrophic. Secondly, the background current caused by the oxidation of steel itself is larger than the magnitude of signal measured from the oxidation of hydrogen atoms (at the 6E12 atoms per second per $cm^2$ level). The signal-to-noise ratio is therefore less than poor. Some patch probe installations include machining the outer surface of the process vessel and then plating palladium on the surface. This has the potential of improving measurements by increasing the atomic hydrogen oxidation efficiency up to near 100% and eliminates the background signal due to oxidation of steel. However, not very many field engineers are willing to allow the external surfaces of their process vessels to be machined in order to apply a patch probe and palladium coating. A final problem with patch probes is the potential for caustic embrittlement that may be caused by the 0.1–0.2 N sodium.hydroxide chemical environment that is in contact with the process vessel walls.

Another method used for the measurement of atomic hydrogen permeation is one in which an airtight seal is installed over an area of the external surface of the process vessel and the buildup in pressure due to the combination of atomic hydrogen to molecular hydrogen at the process vessel surface is measured over time. The method is similar to the in situ hydrogen probes discussed above, but there is no intrusion into the process vessel. One which is used quite extensively in the oil industry is sold under the brand name Beta Foil. The method offers the advantage of nonintrusive measurement, but suffers from the same limitations as the in situ hydrogen probes (including a severe temperature effect) and have not been found to be effective when hydrogen permeation rates are low, as they would be in a well controlled system. In addition, these devices are expensive to install and monitor.

Methods involving electrical measurements of small magnitude can be adversely affected by electrical noise signals in process streams created by pumps, cathodic protection systems, and other electrical equipment which can create electrical signals, in many cases, of equal or greater magnitude than that from the atomic hydrogen permeation being measured.

U.S. Pat. No. 5,405,513 discloses methods and apparatus for laboratory-based measurements in a test cell at, or near, ambient pressure and temperature. The method and apparatus disclosed lacks the capability for the in situ evaluation of actual process streams and vessels where the pressures can be as high as 3000 psi and temperatures reach 300° F./150° C., and therefore cannot be utilized for in situ field applications.

Since the potential for hydrogen damage in a given susceptible steel is directly proportional to the amount of atomic hydrogen diffusing into the steel matrix, a method and apparatus for quantitative measurement of atomic hydrogen diffusion in steel process vessels and pipelines would provide a valuable tool for evaluating the existence and rate of hydrogen damage and the methods undertaken for its control.

It is therefore an object of the invention to provide a method and apparatus for the in situ measurements that will provide a reliable indicator of the atomic hydrogen permeation rate in pipelines and vessels containing process feedstreams.

It is a further object of the invention to provide a method and apparatus for the in situ measurement of corrosion rates under the conditions described above.

Another object of the invention is to provide an electrochemical atomic hydrogen permeation measurement method that is electrically isolated from the process environment.

It is also an object of the invention to provide for such in situ measurements under field conditions of pressures ranging up to 3000 psi and temperatures ranging up to 300° F., or greater.

It is another object of the invention to provide a hydrogen permeation detection probe that can be employed with existing industry standard two-inch access fittings, and further to provide a probe of variable length for use in pipelines and vessels requiring surface mounting and/or insertion of the probe into process streams.

Another important object of this invention is to provide a probe that possesses a high level of installation security and protection against leakage under field conditions prevailing in petrochemical processing facilities.

It is another important object of the invention to provide a probe and a method for its operation that is intrinsically safe and that presents no potential fire hazard.

Yet a further object of the invention is to provide a method and means for accomplishing the above objectives that includes the acquisition and storage of atomic hydrogen permeation data over extended periods of time, and its storage, as for example, on a magnetic recording media, or RAM (random access memory) device, and the downloading and transmission of such stored data into the memory of a general purpose computer at a remote location for subsequent processing and analysis.

SUMMARY OF THE INVENTION

The above objectives and other advantages are achieved in accordance with the apparatus and method of the invention by providing a probe for use in field installations for obtaining data in real time from which data the atomic hydrogen rate of permeation can be determined. The probe comprises an hydrogen damage-resistant metal test specimen electrode of planar configuration having a first face in contact with the process stream, and through which test specimen atomic hydrogen can pass without being trapped. The opposite side, or second face of the test specimen electrode, which is preferably plated with palladium is in contact with an electrolyte solution, such as sodium hydroxide (NaOH) contained in a sealed reservoir. A second counter electrode is positioned proximate the specimen electrode in the electrolyte reservoir, and a voltage potential is established between the electrodes. When atomic hydrogen reaches the palladium surface after permeating the test specimen electrode, it is ionized by the positively charged surface and an electrical current flows between the electrodes. In a preferred embodiment, an external embedded microcontroller is electrically connected to the electrodes. The associated embedded microcontroller monitors and measures the current flow. Data from the embedded microcontroller is stored in digital form and converted by appropriate circuitry into quantitative data that indicates the number of atoms migrating per unit of surface area of the pipeline or vessel.

The test specimen electrode is fabricated from a thin flat sheet of steel that is resistant to hydrogen damage so that hydrogen atoms pass through and are not trapped in the matrix of the steel. In a preferred embodiment, the thickness of the test specimen is in the range from about 0.010 to about 0.050 inches, with a preferred thickness being 0.032 inches. The preferred metal for the test specimen is A106 seamless carbon steel pipe in which a minimum of 10% of the pipe wall thickness has been machined away from both the inner and outer walls of the pipe.

The second, or reservoir side of the test specimen electrode is coated, e.g. by plating, with elemental palladium in order to maximize the atomic hydrogen oxidation efficiency, i.e., the oxidation of hydrogen atoms to hydrogen ions, H+, and to minimize the background current. The H+ ions react with the NaOH ions to form water. Palladium is preferred, since the metal coating significantly enhances the signal produced, as compared to an uncoated specimen. The palladium coating can be applied in as thin a molecular layer as possible, and a thickness of about one-ten thousandths (0.0001) of an inch has been found to perform satisfactorily.

The counter electrode is preferably formed from platinum to maximize the conductivity and measurement of the current flow and avoid any corrosion effect.

After the test specimen has been prepared, its weight is determined so that any change in weight after exposure can be measured. Thus, overall corrosion rate for the duration of the test exposure can be calculated, as well as the instantaneous permeation rate at any given time. Further details and specifications concerning the preparation of the test specimen electrode, as well as the utility and importance of this dual measurement capability is described in U.S. Pat. No. 5,405,513, the disclosure of which is incorporated herein in its entirety by reference.

A reservoir containing sodium hydroxide forms a part of the probe assembly and is in fluid communication with the permeation test specimen. Hydrogen atoms which have permeated the test sample are oxidized to hydrogen ions by the electrochemical conditions present in the cell. The sodium hydroxide in the reservoir then neutralizes the hydrogen ions. The hydrogen permeation rate is determined from the current produced from the electrochemical oxidation of hydrogen atoms. The corrosion rate, which is based on data taken from the corrosion test sample and associated electrodes, is determined by standard methods.

The entire probe assembly is constructed for use with industry-standard access devices that will permit fluid-tight installation at the test site. The probe assembly is isolated from the non-conductive materials to minimize background electrical effects, or noise.

DESCRIPTION OF A PREFERRED EMBODIMENT

Figure 1:
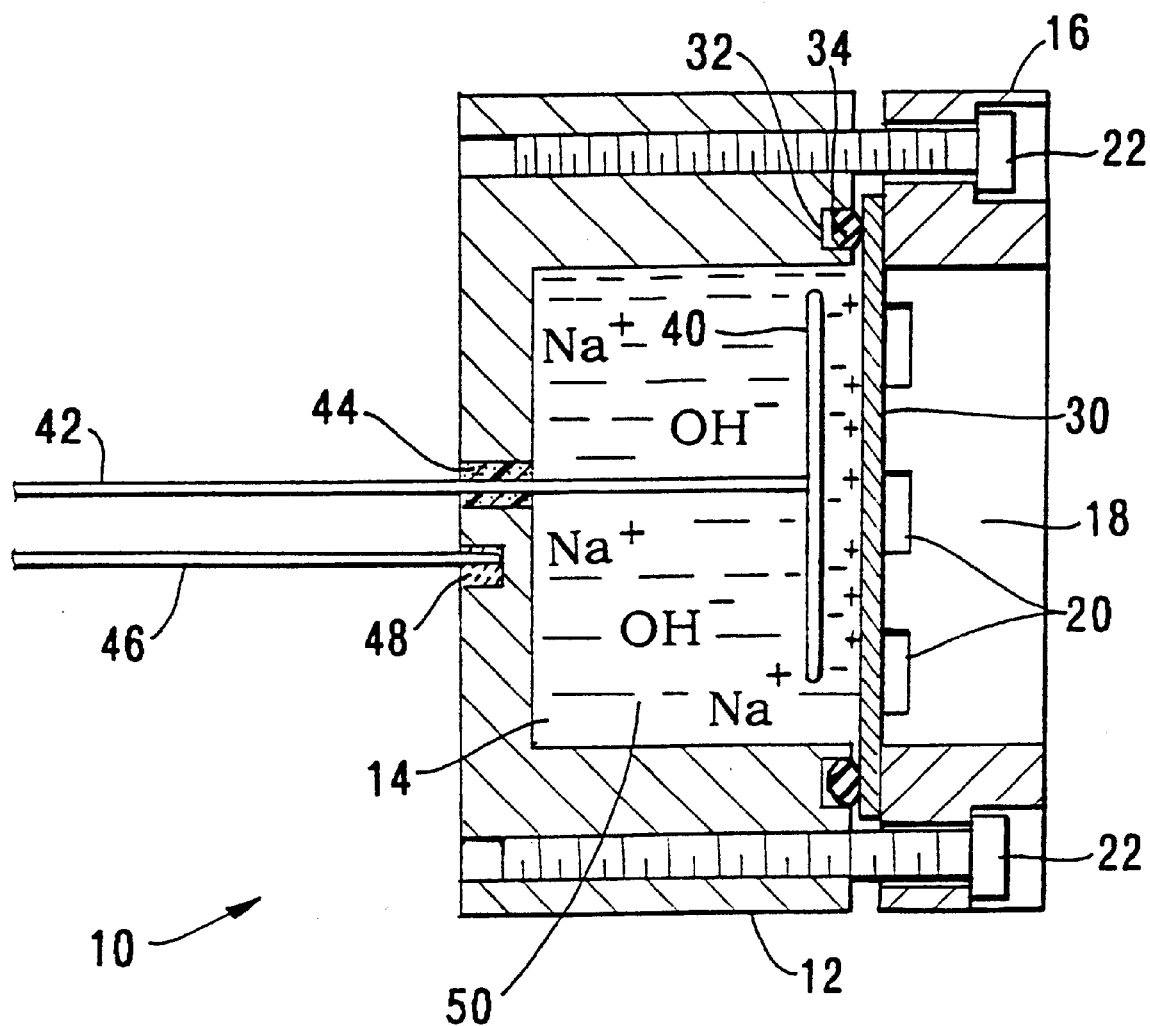
FIG. 1 is a cross-sectional side elevation view of one embodiment of a probe assembly constructed in accordance with the invention.

With reference to the drawings in which like numerals are used to refer to the same elements, FIG. 1 illustrates one embodiment of the probe assembly 10 of the invention, which is comprised of probe body 12 provided with reservoir cavity 14. End clamp 16 is provided with recess 18, the configuration of which corresponds generally to the transverse cross-section of the reservoir 14 with which it is aligned. Clamp 16 forms a protective cover for the very thin electrode 30. A plurality of fluid passageways 20 around the periphery of clamp 16 permit the process fluid to flow through recess 18. The probe body 12 and clamp 16 are preferably fabricated from a corrosion-resistant material such as stainless steel and Hastalloy C-276 to prolong their life in highly corrosive environments. The reservoir body and other structural members of the probe can alternatively be fabricated from engineering plastics and rigid polymer compositions known to the chemical process arts.

Test specimen electrode 30 is positioned over the open end of reservoir 14 in fluid-tight sealing relation, e.g., by means of O-ring 34 that is received in groove 32 in body 12. Electrode 30 is retained in this position by clamp 16 that is secured to probe body 12, e.g., by a plurality of corrosion-resistant threaded fasteners 22 around the periphery of the clamp. As will be apparent to one of ordinary skill in the art, the clamp can be secured to the body by other means, such as by providing male and female threads at the periphery of these parts so that the clamp is screwed onto the body.

It will be appreciated that the test specimen electrode 30 is susceptible to damage in the field environment. Thus, in addition to holding the test specimen electrode 30 in fluid-tight alignment with the reservoir, the clamp 16 protects electrode 30 from damage before, during and after its contact with the process stream.

In the preferred embodiment, where the probe assembly 10 is configured for use with a standard two-inch diameter access device, the test specimen electrode 30 measures about 1.0 inch in diameter and is about 0.032 inches thick, including its palladium coating that is plated to a thickness of about 0.0001 inches.

As also shown in FIG. 1, counter electrode 40 is positioned in the reservoir 14 proximate test electrode 30, the palladium-coated side of which is in contact with electrolyte solution 50. Counter electrode 40 is preferably made of platinum and includes conductor 42 which passes in non-conducting relation through orifice 44 in probe body 12. Counter electrode conductor 42 is conveniently held in position by a non-conductive, insulating bedding sealant, such as epoxy resin, that will not react with the electrolyte solution.

In order to complete the electric circuit between electrodes 30 and 40, conductor 46 is bonded to body 12, as by soldering it into position in orifice 48.

Figure 2:
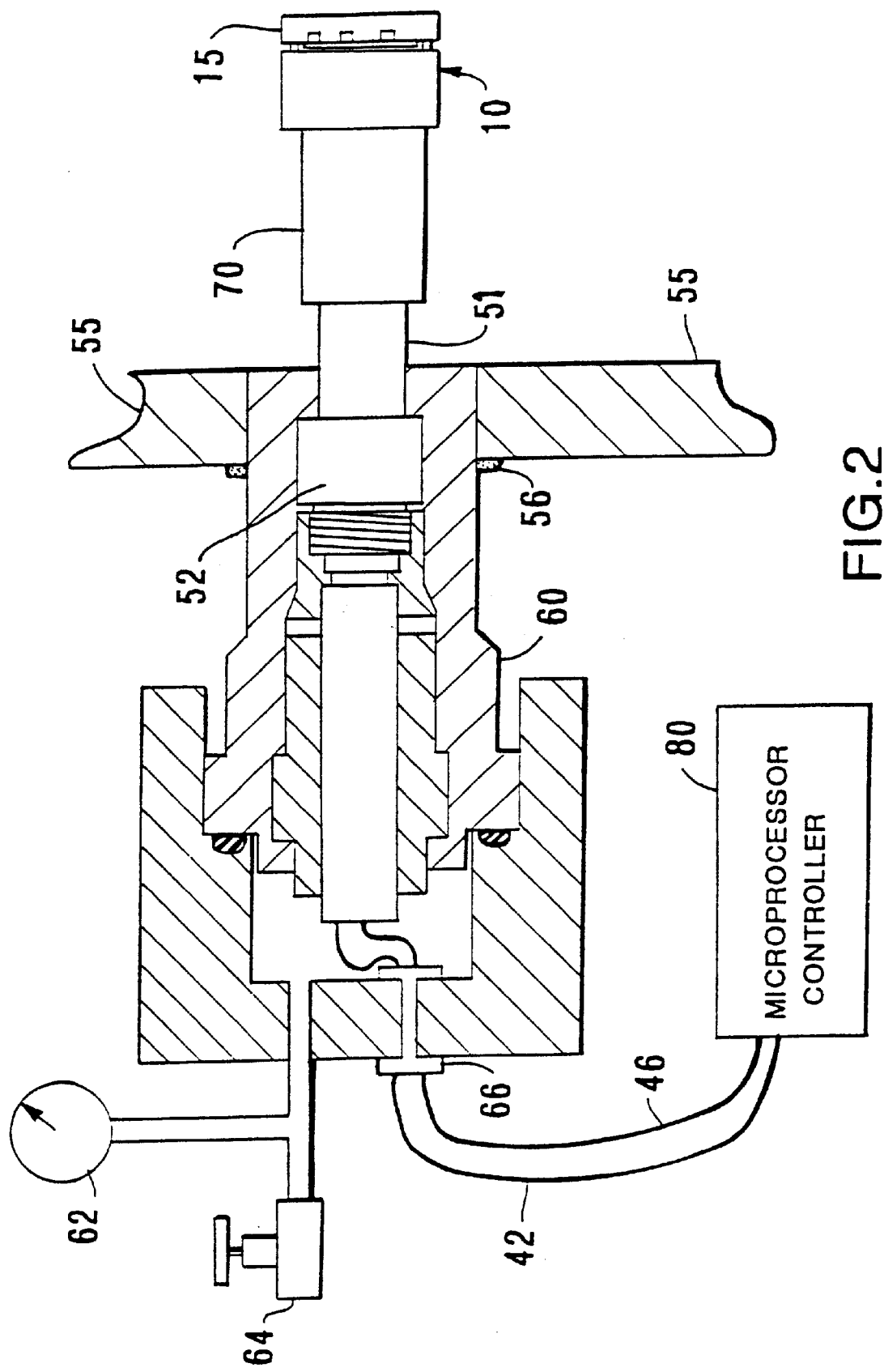
FIG. 2 is a side elevation view in partial section of the probe assembly of FIG. 1 in a typical field installation.
Figure 3:
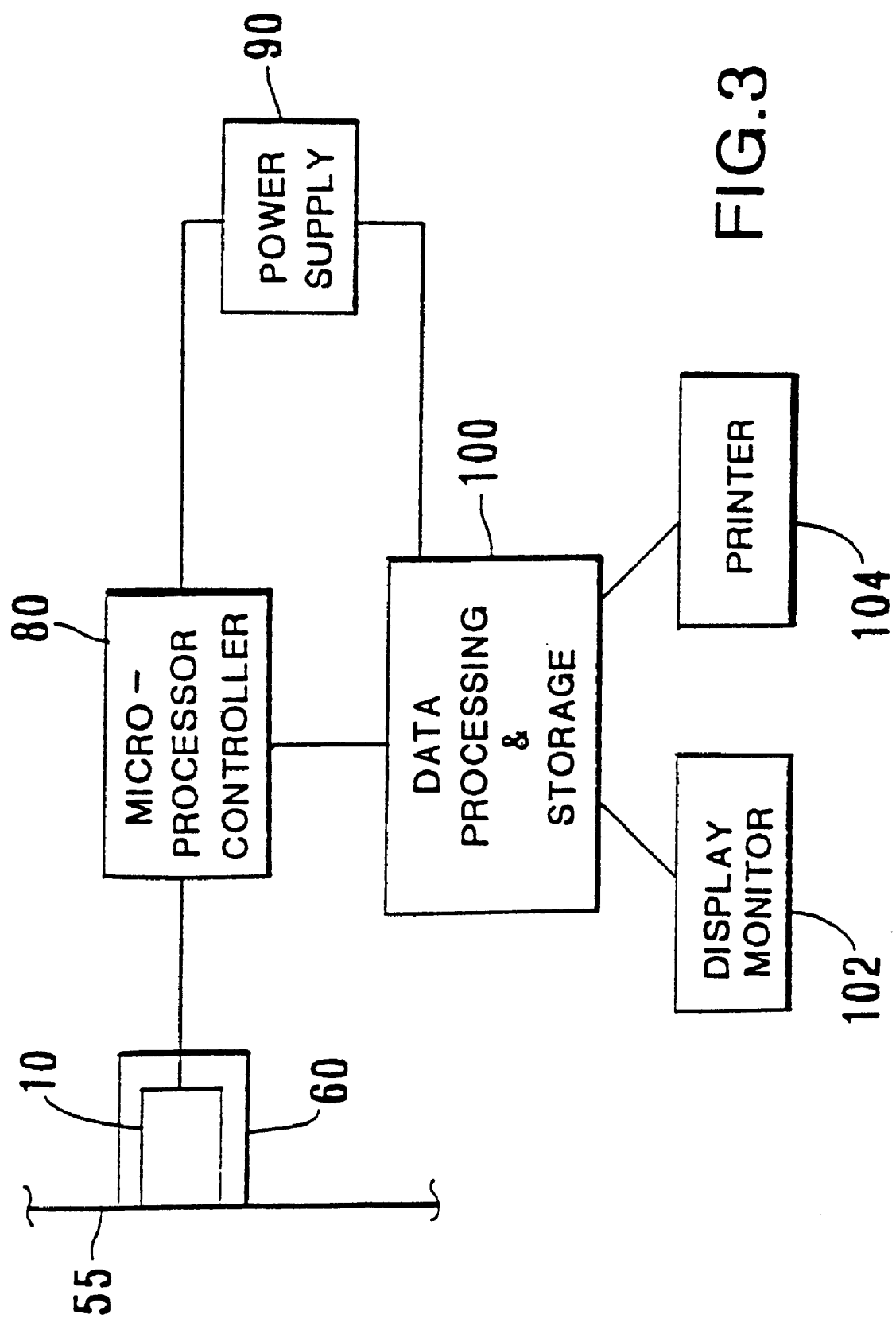
FIG. 3 is a schematic view illustrating one embodiment utilizing the method and apparatus of the invention.

As illustrated in the embodiment of FIG. 2, the probe assembly 10 can be positioned in contact with. the process fluid, as by passing it through a fluid-tight access device fitting 60 in a pipeline or vessel wall 55. A suitable device is sold by Rohrback-Cosasco, and is described below.

Probe assembly 10 is securely mated in fluid-tight relation with insulator 70 to electrically isolate the probe from the pipeline and all other sources of stray electrical currents. Insulator 70 can conveniently be made from any of various commercially available non-conducting engineering plastics, such as Torlon®, in the form of a casting or a machined part having a central orifice for passing conductors 42 and 46 from the counter and test specimen electrodes.

Insulator 70 is mated to extension conduit 51 which in turn is mated to seal 52. In a preferred embodiment, seal 52 comprises a high pressure electrical feed through to provide an additional measure of safety and to minimize any fire hazard associated with electrical devices. It will be understood that extension conduit 51 can be of any desired length, and its length is determined by the desired position of the distal end 15 of probe assembly 10 with respect to the interior surface of the pipe or vessel wall. The probe can be fitted with components of different lengths so that it can be flush-mounted with the walls of a vessel or extend any desired length into the process stream.

The position of the probe with respect to the side wall depends on the application. For example, in an oil field pipeline where the pipe is scraped internally three times per week, the probe cannot extend beyond the internal surface of the pipeline or it will be torn off by the scraper. For this application, a flush-or surface-mounted installation is required. The same considerations apply if the probe 10 is to be inserted into an access fitting in a pipeline, and the pipeline is subject to the periodic passage of an inspection tool. In this application, the probe must also be mounted approximately flush with the interior surface of the pipe wall.

In other installations and applications where it is desirable to have the probe 10 extend down into a vessel, e.g., 24", a longer piece of ½" stainless steel pipe can be placed as an extension between the Torlon® isolator and the probe extension. As will be apparent to one of ordinary skill in the art, the dimensions of all of the elements will be proportioned accordingly.

In an alternative embodiment of the invention, the tip of the probe is provided with a cover that will prevent direct contact of the test specimen with foreign objects prior to and after installation. The protective cover is provided with channels to permit the process fluid to contact the exterior surface of the test specimen electrode 30.

The entire tip 15 of the test electrode is exposed to the process stream. In the preferred embodiment that is adapted for use with an industry-standard 2" access fitting, the probe clamp 16 has a 1.89 mm/0.744" diameter orifice that communicates directly with the surface of the test specimen and provides an exposed surface area of about 2.8 cm$^2$. The fluid passage ways or channels 20 in the probe clamp 16 permit the process stream to flow directly across the surface of the test specimen electrode 30.

The access fitting 60 can be selected from any of the several devices that are commercially available and in wide-spread industrial use. One such device that has been generally accepted in the petroleum industry is sold by Rohrback Cosasco Systems, Inc. of Santa Fe Springs, Calif., under the trademark COSASCO®. As shown in FIG. 2, this and like devices are permanently affixed to the exterior of the pipe or vessel wall 55 by weldments 56. The access device 60 is also provided with pressure indicator 62 and pressure release valve 64, as well as pressure-tight electrical connector 66 to provide fluid tight passage of the electrical connection of electrode conductors 42 and 46.

In a preferred embodiment, the electrodes are electrically connected to embedded microcontroller 80, which is an appropriately programmed microprocessor and controller with solid state memory devices. The electrical connections are made to a solar electrical power supply 90. A solar power source is preferred, since it requires no electrical connection to the process environment in which current flow can take place and interfere with the small magnitude measurements of the invention. Alternatively, power can be supplied from conventional sources, such as a main, or via batteries charged by solar-powered collectors. The latter power source can be effectively and cost-effectively employed under field conditions where the installation is in a geographically remote location where electrical service is not conveniently available.

In the practice of the method of the invention, the reservoir 14 is filled with a 0.10 Normal (0.10N) solution of reagent grade sodium hydroxide in distilled water, and the probe assembly 10 is secured in position in a previously installed access device 60 in a vessel or pipeline wall 55. Under field conditions, the reservoir will require servicing to replenish the reagent about every 30 to 45 days. The reservoir is filled using an eyedropper, pipette, or similar dispensing device.

The microprocessor and controller 80 maintains a fixed potential very near to the surface of test specimen electrode 30 to effect the instantaneous oxidation of hydrogen atoms and to accurately measure the electrons released during oxidation and corresponding current flow, to store the data in digital form in its RAM device, and to download the stored data from the RAM device, e.g., via standard RS-232 format, when instructed by the data processing and storage means 100.

In a preferred embodiment, the probe assembly is adapted to receive a hydrogen permeation test that is exposed to the process environment.

The data collected is transmitted to a data storage device and/or to a general purpose computer that is appropriately programmed to process and display the desired permeation and corrosion rate information. Data can be gathered periodically or continuously, and stored locally for later transmission to a central storage and processing facility.

In a preferred embodiment, the electronic portion of the invention is comprised of the three printed circuit boards, designated as the Power Supply board, the hydrogen Permeation Probe Microprocessor board, and the Hydrogen Permeation Analog Control board. The individual electronic components are selected for their electrical characteristics as well as their ability to withstand high service temperatures which are sometimes encountered in field locations. The electronic housing enclosure is sealed from the environment to protect the electronic components. The apparatus can be powered by either 110 VAC mains power, or by battery or solar power.

As noted above, atomic hydrogen can produce various types of damage to process facilities, including loss of ductility and strength, hydrogen blistering and hydrogen-induced cracking, other damage due to high-temperature effects. The method and apparatus of the invention can be used to collect data for evaluating and predicting the effects in all of these hydrogen damage processes except for those high-temperature effects which occur at temperatures exceeding the performance capability limit of the invention.

We claim:

1. An apparatus for detecting atomic hydrogen created in a carbon steel pipeline containing a moving process stream at pressures up to 3000 psi and temperatures up to 300° F., by accessing the process stream through the pipeline wall at a location having an access fitting, said apparatus comprising:

(a) a probe assembly including:

a fluid-tight reservoir body for containing a liquid electrolyte, a set of electrodes consisting of a test specimen electrode comprising a planar member of a metal through which atomic hydrogen can pass without being trapped, said planar member being mounted to said reservoir body and having a palladiumcoated interior surface positioned for contact with the electrolyte and an exterior surface exposed externally of said reservoir body, and a counter electrode mounted proximate the test specimen electrode to the interior of said reservoir body for contact with the electrolyte, and electrical leads having first ends attached to said test specimen electrode and said counter electrode, respectively;

(b) a mounting assembly for fluid-tight coupling with the access fitting, said probe assembly being secured to said mounting assembly such that when said mounting assembly is coupled with the access fitting said probe assembly is positioned internally of the pipeline wall with said exterior surface of said test specimen electrode in contact with the process stream, wherein said mounting assembly provides access to second ends of said electrical leads externally of the pipeline wall and includes an isolator for electrically insulating said probe assembly from the pipeline wall; and (c) electrical circuitry connected to said second ends of said electrical leads for ionizing hydrogen atoms passing to the interior surface of said test specimen electrode from the process stream, wherein said electrical circuitry maintains a fixed potential between said test specimen electrode and said counter electrode, to thereby create between said test specimen electrode and said counter electrode a current flow indicative of the number of hydrogen atoms in the process stream.

2. The apparatus of claim 1, wherein the liquid electrolyte is an aqueous solution of sodium hydroxide.

3. The apparatus of claim 1, wherein the probe assembly will pass through a two-inch access fitting through which access is provided to the process stream.

4. The apparatus of claim 3, wherein:

said reservoir body is generally cylindrical with a diameter of less than two inches for passage through the opening in the access fitting;

said test specimen electrode forms a distal end of the reservoir body;

said mounting assembly includes a mounting arm for securing the apparatus in the access fitting; and said isolator comprising a non-conducting plastic member interposed between said mounting arm and a proximal end of said reservoir body.

5. The apparatus of claim 4, wherein said mounting assembly includes an extension member for varying the position of the exterior surface of said test specimen electrode in the process stream.

6. The apparatus of claim 5, wherein said extension member is detachably connected between said mounting arm and said isolator.

7. The apparatus of claim 4, wherein said isolator and said mounting arm have internal passages for said leads and said mounting assembly includes a high-pressure seal through which said leads pass from said passages to the exterior of the pipeline.

8. The apparatus of claim 1, wherein said counter electrode comprises a planar member of platinum.

9. The apparatus of claim 1, wherein said reservoir body is a made of a high-strength, nickel-based corrosion resistant alloy or a rigid polymer.

10. The apparatus of claim 1, wherein said reservoir body has an open side and said probe assembly further includes a clamp secured to said reservoir body to hold said test specimen electrode in place covering said open side of said reservoir body.

11. The apparatus of claim 10, wherein said probe assembly further includes a cover for protecting said test specimen electrode, said cover including channels for permitting the process stream to contact said exterior surface of said test specimen electrode.

12. The apparatus of claim 10, wherein:

said reservoir body is electrically conductive and said first end of one of said electrical leads is secured to said reservoir body to complete an electric circuit therebetween;

said clamp holds said test specimen electrode in electrically conductive contact with said reservoir body; and said counter electrode is mounted to said first end of the other said electrical lead and said counter electrode is held in position within said reservoir body by securing said counter electrode to an orifice in said reservoir body with an electrically nonconducting adhesive.

13. The apparatus of claim 1, wherein said electrical circuitry includes a microprocessor controller for measuring the current flow between said test specimen electrode and said counter electrode.

14. The apparatus of claim 13, wherein said microprocessor controller includes a memory for storing data related to the current flow.

15. The apparatus of claim 14, wherein said microprocessor is programmed to record and store the data over time in said memory.

16. The apparatus of claim 15, wherein said microprocessor is programmed to record and store the data intermittently.

17. The apparatus of claim 15, wherein said memory includes a magnetic storage medium.

18. The apparatus of claim 15, wherein said memory includes a semiconductor device.

19. The apparatus of claim 14, wherein said electrical circuitry includes electronic access and computing means remote from said microprocessor controller and said microprocessor controller is programmed for periodically transferring data to said electronic access and computing means.

20. The apparatus of claim 13, further comprising a power supply for providing electrical power to said electrical circuitry, said power supply being selected from the group consisting of a solar collector, a battery and a combination of a solar collector and a battery.

* * * * *